(12) United States Patent  
Moore et al.

(10) Patent No.: US 8,210,028 B2
(45) Date of Patent: Jul. 3, 2012

(54) METHODS AND APPARATUS FOR EXTRACTION OF PARTICLES FROM SURFACES

(76) Inventors: Robert R. Moore, Vancouver, WA (US); David Blessing, Vancouver, WA (US)

( * ) Notice: Subject to any disclaimer, the term of this patent is extended or adjusted under 35 U.S.C. 154(b) by 691 days.

(21) Appl. No.: 12/247,375

(22) Filed: Oct. 8, 2008

(65) Prior Publication Data

US 2009/0250382 A1  Oct. 8, 2009

Related U.S. Application Data

(60) Provisional application No. 60/978,308, filed on Oct. 8, 2007, provisional application No. 60/978,242, filed on Oct. 8, 2007.

(51) Int. Cl.
*G01N 37/00* (2006.01)
(52) U.S. Cl. .................................................. 73/28.01
(58) Field of Classification Search ................. 73/28.01, 73/28.03
See application file for complete search history.

(56) References Cited

U.S. PATENT DOCUMENTS

| | | | |
|---|---|---|---|
| 4,987,286 A * | 1/1991 | Allen ........................ | 219/121.68 |
| 4,987,767 A * | 1/1991 | Corrigan et al. ............. | 73/23.36 |
| 5,465,828 A * | 11/1995 | Thomas et al. ............... | 198/495 |
| 5,915,268 A * | 6/1999 | Linker et al. .................. | 73/23.2 |
| 5,942,699 A * | 8/1999 | Ornath et al. ............. | 73/863.21 |
| 6,324,927 B1 * | 12/2001 | Ornath et al. ............. | 73/864.33 |
| 6,506,345 B1 * | 1/2003 | Lee et al. ........................ | 422/70 |
| 6,764,386 B2 * | 7/2004 | Uziel ............................. | 451/39 |
| 6,864,458 B2 * | 3/2005 | Widmann et al. ........ | 219/121.69 |
| 7,029,921 B2 * | 4/2006 | Lee et al. ....................... | 436/148 |
| 7,543,478 B2 * | 6/2009 | Burroughs et al. .......... | 73/28.01 |
| 2002/0029956 A1 * | 3/2002 | Allen ....................... | 204/157.15 |
| 2007/0220953 A1 * | 9/2007 | Perry et al. .................... | 73/28.01 |
| 2008/0250845 A1 * | 10/2008 | Burroughs et al. .......... | 73/28.01 |

* cited by examiner

*Primary Examiner* — John Fitzgerald

(57) ABSTRACT

A method and apparatus for the extraction of particles from surfaces is disclosed. A preferred method comprises the steps of (1) adjusting the temperature and humidity of an air supply to provide an adjusted air supply, (2) directing a blast from the adjusted air supply to a surface bearing particles, so as to produce a deflected blast that comprises some of the particles from the surface, (3) collecting the deflected blast and particles, and (4) directing the deflected blast and particles towards an analyzer. A preferred apparatus includes an air adjuster and a probe comprising an adjusted air supply passage, an adjusted air aperture, a deflected air aperture, and a deflected air passage, wherein the air adjuster is adapted to provide a flow of adjusted air to the adjusted air supply passage and the adjusted air aperture.

20 Claims, 4 Drawing Sheets

Humid Air Extraction Efficiency of
PETN Alternate Explosives

| Description | Room Air | Hot Humid Air |
|---|---|---|
| Particles IJAG Deposited with Fluorescent Dye (Before extraction): | 584 | 342 |
| Fluorescent Particles Humid Air Remaining (after Extraction): | 453 | 138 |
| Explosive Particles Blown Off | 131 | 203 |
| Extraction Efficiency of IJAG-deposited PETN Particles | 22% | 60% |
| Total number of Captured Particles | 12 | 40 |
| Capture Efficiency of Extracted Particles | 9% | 20% |

FIG. 4

METHODS AND APPARATUS FOR EXTRACTION OF PARTICLES FROM SURFACES

BACKGROUND OF THE INVENTION

The fields of the invention are methods and apparatus for sampling particles on surfaces to allow for the detection of hazardous particles. The prompt detection of hazardous particles is advantageous in a number of situations. For example, terrorists and others may seek to destroy commercial aircraft by placing explosives into luggage and other containers taken onto the aircraft, and subsequently detonating the explosives. One approach to avoiding such attacks is to screen all persons and containers before they are onboard the aircraft. If a person has been handling explosives, then particles of the explosive may be present on the person's hands and clothing. If there is an explosive in a piece of luggage or other container, then explosive particles may be present on the exterior of piece of luggage or other container. Current detection methods include wiping the exterior of luggage and other containers with a swab, and then inserting the swab into an analyzer which is adapted to detect any explosive particles on the swab. Current detection methods also include placing a person in an air booth which directs blasts of air at the person, and collects the deflected blasts of air, and delivers the deflected air to an analyzer which is adapted to detect any explosive particles in the deflected air.

However, there are limitations on current detection methods and apparatus. The current methods and apparatus may involve a significant delay and inconvenience, from the perception of passengers who are seeking to board commercial aircraft. In addition, the detection capability of current detection methods and apparatus leaves room for improvement.

In the fields of inventions, the particles of interest may be solids, or semi-solids, or small droplets of liquid. These particles of interest may be hazardous, or indicative of hazardous materials, or may be disguised particles. A disguised particle may be a hazardous substance that is coated with a non-hazardous material in an attempt to avoid detection, and in such circumstance the hazardous material may be referred to as the payload.

In the fields of invention, the hazardous particles may be explosives, poisons, toxins, biological materials, radioactive substances and other weapons of mass destruction. These explosives may fall into different categories. For example, nitroglycerine may be regarded as an ester, TNT may be regarded as an aromatic, and RDX may be regarded as a nitramine. There are also peroxide explosives, such as HMTD, TATP, DADP and TMDD.

There are a number of known methods and apparatus to analyze particles, and determine whether the particles are hazardous materials. These include infrared (IR) spectroscopy, and Raman spectroscopy, as well as others.

SUMMARY OF THE INVENTION

The invention comprises methods and apparatus for the extraction of particles from surfaces. A preferred method according to the present invention comprises the steps of (1) adjusting the temperature and humidity of an air supply to provide an adjusted air supply, (2) directing a blast from the adjusted air supply to a surface bearing particles, so as to produce a deflected blast that comprises some of the particles from the surface, (3) collecting the deflected blast and particles, and (4) directing the deflected blast and particles towards an analyzer. The temperature is preferably adjusted to be above the ambient temperature, and below the upper limit based upon materials and pain threshold. The humidity is preferably adjusted above the ambient but below the dew point.

A preferred apparatus according to the present invention includes an air adjuster and a probe comprising an adjusted air supply passage, an adjusted air aperture, a deflected air aperture, and a deflected air passage, wherein the air adjuster is adapted to provide a flow of adjusted air to the adjusted air supply passage and the adjusted air aperture. The flow may be continuous, intermittent, pulsed or periodic. The adjusted air aperture and a deflected air aperture are configured in proximity to allow a blast of adjusted air from the adjusted air aperture to impact an adjacent surface containing particles. The blast dislodges particles from the surface. The deflected air passage and deflected air aperture are adapted to receive the deflected blast and dislodged particles, and direct them to an analyzer. In another embodiment of the invention, one may adjust the angle at which the a blast of adjusted air impacts the surface containing particles.

BRIEF DESCRIPTION OF THE DRAWINGS

FIG. 4 is a table showing a comparison of extraction of PETN explosive particles from a surface using room air and hot humid air.

DETAILED DESCRIPTION OF THE INVENTION

Figure 1:
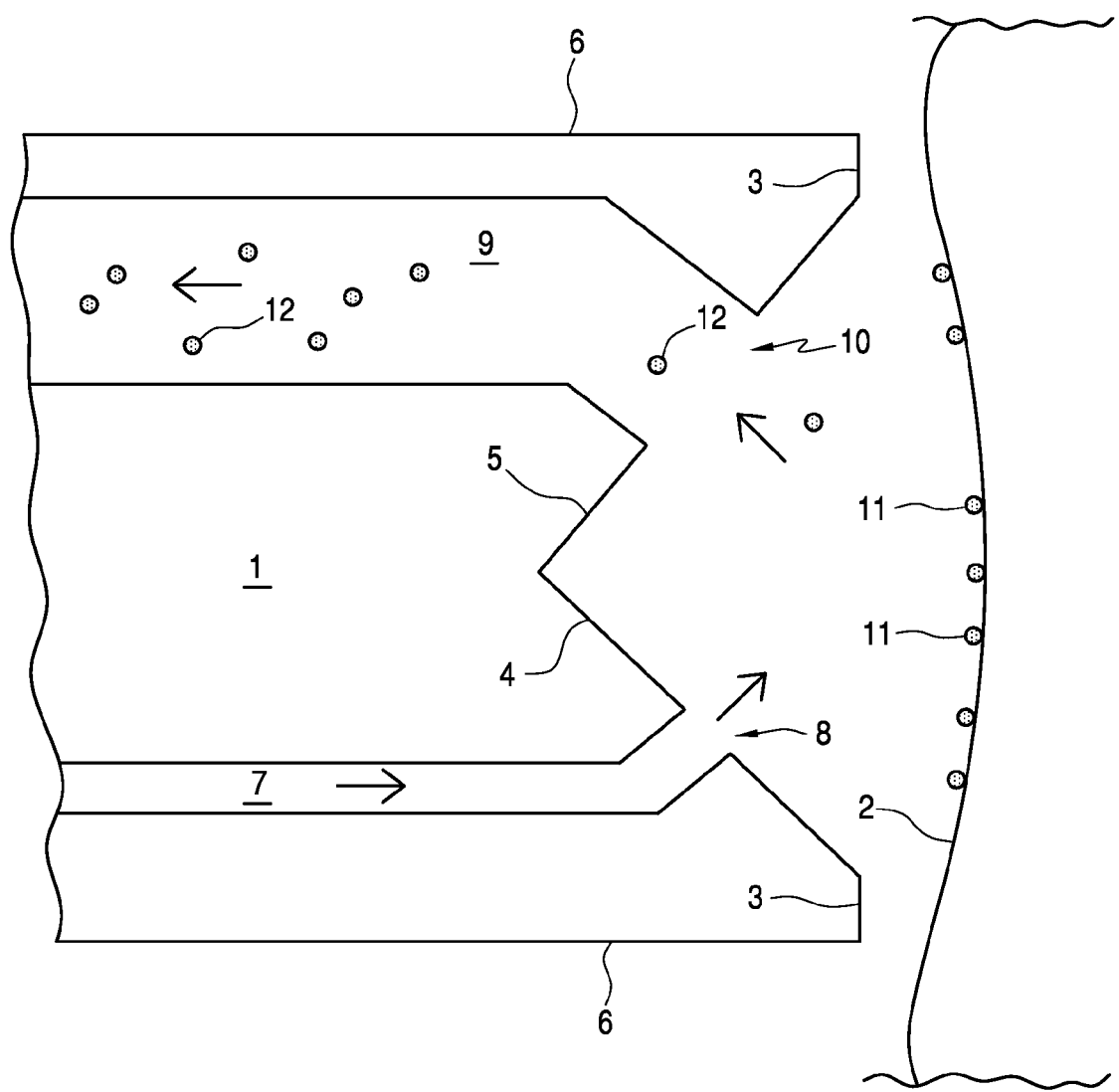
FIG. 1 is a schematic cross section of a probe adjacent a surface containing particles.
Figure 2:
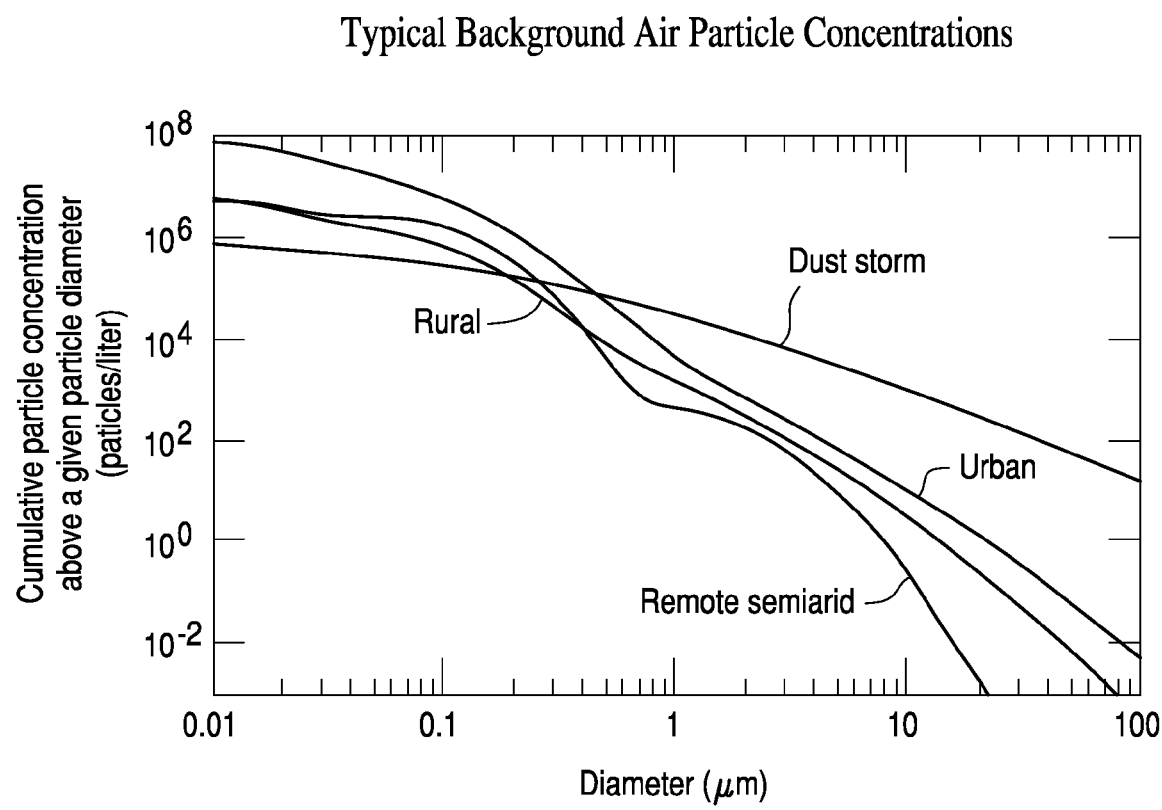
FIG. 2 is a table showing typical background air particle concentrations.
Figure 3:
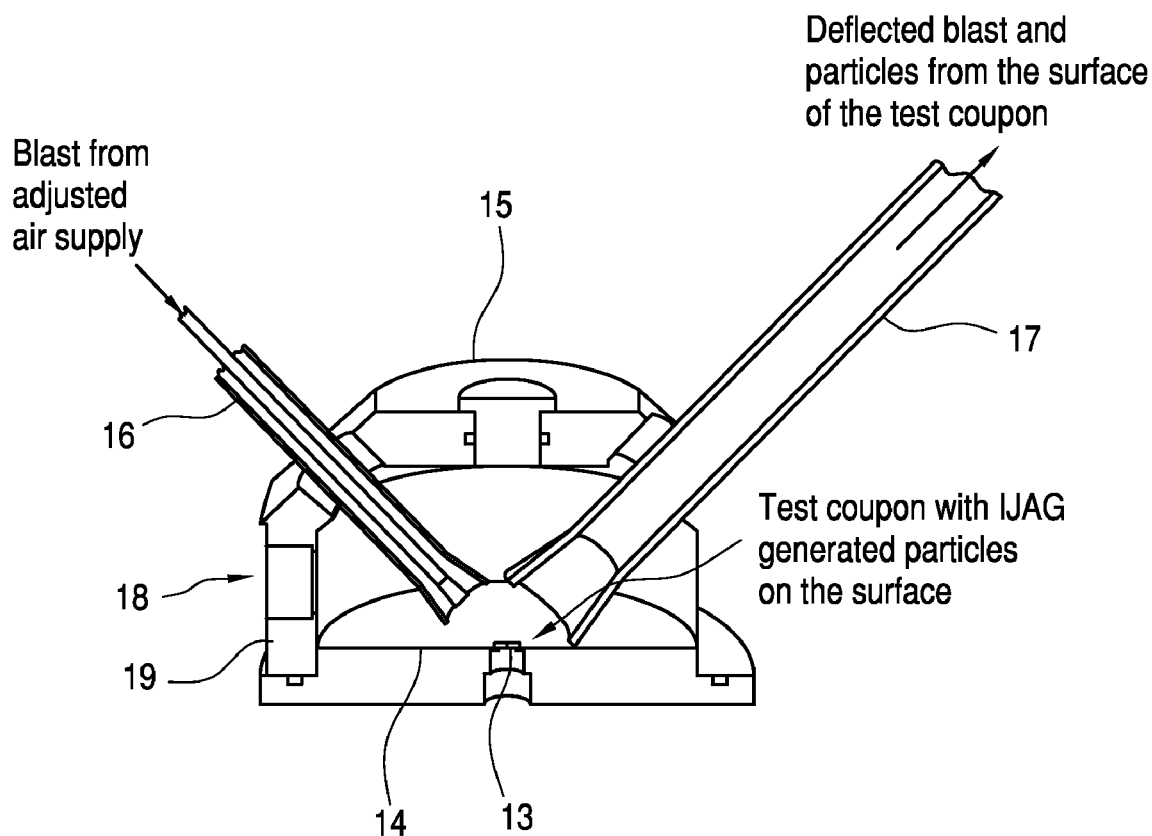
FIG. 3 is schematic cross section of a testing apparatus.

FIG. 1 shows a probe 1 adjacent to a surface 2 in schematic cross section. Probe 1 has periphery 3 which may be relatively planar as shown, or curved or pointed. Periphery 3 extends from the exterior 6 of probe 1. The periphery 3 is adapted to contact, or to come in close contact with the surface 2. The periphery 3 should be adjusted depending on the surface 2. For example, if the surface 2 is of vinyl luggage, the periphery 3 should be designed so that it does not cut the vinyl luggage if the periphery 3 comes into contact with the surface 2. First wall 4 extends from periphery 3 and is provided with adjusted air aperture 8 which is the terminus of adjusted air supply passage 7. Adjusted air aperture 8 may be of the same dimensions of adjusted air supply passage 7, or may be of restricted size.

A source of an adjusted air supply (not shown) is connected to adjusted air supply passage 7. Adjusted air is forced through adjusted air supply passage 7, through adjusted air aperture 8, and blasted onto surface 2. The adjusted air may be forced by any of a number of means. For example, a fan may blow adjusted air into adjusted air supply passage 7, or a pump may pump adjusted air into adjusted air supply passage 7.

In one embodiment, the source of air may be the ambient, and a fan or blower draws air from the ambient, and forces the air through an air adjuster (not shown). The air adjuster may increase the temperature and/or humidity of the input, and deliver an adjusted air supply as the output. This force may propel the output through adjusted air supply passage 7 and adjusted air aperture 8 and blast onto surface 2.

The air adjuster may comprise any of a number of apparatus known to the art, including electric resistance heaters and humidifiers. The temperature is preferably adjusted to be above the ambient temperature, and below the upper limit.

The upper limit may depend on the surface. If the surface is human skin, then the upper limit is the pain threshold (the temperature at which an average persons feels pain from the temperature of the air), which may be about 104° F. If the surface is an object, then the upper limit is the lower of the temperature at which the surface degrades or melts, and the temperature at which the particle of interest degrades, melts or produces an adverse reaction (e.g., bonds to the surface, or becomes plastic and smears across the surface rather than dislodging). The humidity is preferably adjusted above the ambient but below the dew point. Increased humidity may increase the efficiency of the extraction, but condensation is not desirable. Thus, when ambient air is used, the upper limit of the adjustment of humidity may change as the humidity of the ambient air changes humidity. In one embodiment, the air adjuster provide a continuous flow of adjusted air to air supply passage 7. In other embodiments, the air adjuster may provide an intermittent, pulsed or periodic flow of adjusted air to the air supply passage 7. In other embodiments, the air adjuster may be integrated into the probe.

In another embodiment, the source of adjusted air may be a pressurized gas cylinder, and the pressure differential with the ambient may cause adjusted air to flow through adjusted air supply passage 7, through adjusted air aperture 8, and blast onto surface 2. The adjusted air supply should be of sufficient pressure to cause the velocity of the gasses flowing through adjusted air aperture 8 to be great enough to overcome the forces holding the particle to the surface (e.g., gravity, adhesive forces), and entrain the particle into the flowing gas. For example, to dislodge particles consisting of nitrosyl containing compounds (such as explosives) on a glass surface, an adjusted air velocity of greater than 30 meters per second may be necessary.

The term air should be understood to include not only air from the ambient, but also compressed air in a pressurized gas cylinder, or compressed air from another source. In addition, the term air should be understood to include other suitable gases. For example, there may be circumstances where a gas such as pure nitrogen may adjusted as to temperature and humidity, and used to blast the particles from the surface. Additionally, other suitable gases should be understood to include gases, vapors, and aerosols. Suitable gases may contribute to the release of particles from a surface by physical, chemical, or electronic means. Such gases may affect the surface, or the particles, or both. For example, such gases may alter the hydrogen bonding of the particle to the surface it is deposited on, making particle detachment from the surface happen more readily. The gases may also alter the surface energy of the surface the particles are adhered to, or the surface energy of the particles themselves, again making particle detachment from the surface happen more readily.

A plurality of particles 11 are adhered to surface 2. The blast of adjusted air from adjusted air aperture 8 onto surface 2, extracts some of adhered particles. Surface 2 deflects the blast from adjusted air aperture 8 towards deflected air aperture 10 in second wall 5 which extends from first wall 4 to the periphery 3 of probe 1. The deflected blast containing extracted particles 12 flows through deflected air aperture 10 in second wall 5 and into deflected air passage 9 which carries the extracted particles 12 to an analyzer (not shown). Deflected air aperture 10 is usually of larger diameter (or area) as compared to adjusted air aperture 8.

Other configurations may be used. For example, the adjusted air supply passage may in the center of the probe, and surrounded concentrically by the deflected air passage. As another example, if the surface is cloth or a screen, then the deflected air passage and the deflected air aperture may be opposed to the adjusted air supply passage and the adjusted air aperture. A third example of an adjusted air supply passage is an extendable, flexible or rigid enclosure around the extraction area and close to the surface to improve capture performance and minimize extraction of fugitive particles either from the surrounding air or neighboring surfaces.

FIG. 2 is a table of the size of particles that may be found in different ambient air sources. In some circumstances, it may be preferable to filter the ambient air, before the ambient air is supplied to the air temperature and/or humidity adjuster.

FIG. 3 shows a testing apparatus in schematic cross section. This testing apparatus may be used to compare the apparatus and methods of the present invention, to the prior art apparatus and methods. Test coupon 13 may be placed on surface 14 of testing apparatus 15. Supply tube 16 may be attached to either an ambient air supply, and an adjusted air supply, and directs a blast of the same onto test coupon 13. The deflected blast and particles dislodged from coupon 13 are carried by exit tube 17. Coupon 13 is within a generally closed test chamber that is provided with vent 18 in the side wall 19 of the test chamber to prevent any pressure build up in the test chamber.

FIG. 4. presents the results of tests that were carried out with the apparatus shown in FIG. 3. The extraction with hot humid air achieved an extraction efficiency of 60%, while the extraction with ambient air achieved an extraction efficiency of 22%.

The present invention provides significant improvements over the prior art. In another test, the prior art swab method detected 23% of bacterial spores on a surface, but the present invention detected 94% of the bacterial spores. In yet another test, the prior art air booth method detected 1% of the particles TNT on a surface, but the present invention detected 64% of the particles of TNT on the surface.

The present invention is expected to provide significant advantages over the prior art in regard to hazardous particles that are explosives, or related to explosives. These explosives include nitroglycerine, TNT, RDX, HMTD, TATP, DADP and TMDD.

Example 1

In this example, 266 Semtex explosive particles were deposited onto a glass test coupon. The test coupon was placed into the test apparatus. The supply tube of the test apparatus was connected to an adjusted air supply consisting of 40° C. air at 80-90% relative humidity, and was pressurized to 25 psi which resulted in a 37 m/s gas velocity. The adjusted air supply was activated for a period of 60 seconds. After this extraction operation, 96 Semtex particles remained on the test coupon, yielding an extraction rate of 64%.

Example 2

In this example, 108 C-4 explosive particles were deposited onto a glass test coupon, which was then placed into the test apparatus. The supply tube was connected as in Example 1. After a 60 second extraction period, 65 C-4 particles remained on the test coupon, yielding an extraction rate of 40%.

Example 3

In this example, 239 TNT particles were deposited onto a glass test coupon, which was then placed into the test apparatus. The supply tube was connected to an adjusted air supply consisting of 43° C. air at 5% relative humidity, and was pressurized to 25 psi which resulted in a 37 m/s gas velocity. After a 60 second extraction period, 224 TNT particles remained on the test coupon, yielding an extraction rate of 3%.

Subsequently, 224 TNT particles were deposited onto a glass test coupon, which was then treated as before, except the relative humidity of the adjusted air supply was raised to 90% RH. After a 60 second extraction period, 39 TNT particles remained on the test coupon, yielding an extraction rate of 83%.

Example 4

Future embodiments of the device could be configured in an air shower type arrangement, with multiple adjusted air apertures to dislodge particles from the surfaces of large objects. Such objects may be alive as in the case of humans, or inanimate as in the case of a pallet of shipped goods. Adjusted air parameters will be adjusted as appropriate for the object being interrogated. This may include, but is not limited to, increasing the temperature of the adjusted air to a temperature greater than ambient, and increasing the relative humidity to a level greater than ambient. Adjusted air pressure will be modified as necessary to achieve sufficient air velocities with the apertures used. Resulting adjusted air flows may be greater than 1000 liters per minutes. Rates of particle dislodgement are expected to be similar to rates observed in the test apparatus.

The present invention is not to be limited by the foregoing specification, and the associated drawings, but only by the following claims, because one of ordinary skill in the art could readily adapt the invention beyond the express disclosure of the specification and drawings.

We claim:

1. A method of extraction of particles from a surface comprising the steps of
   (1) adjusting a temperature and a humidity of an air supply to provide an adjusted air supply,
   (2) directing a blast from the adjusted air supply to a surface so as to produce a deflected blast, wherein said surface comprises a first particle before the blast, and the deflected blast comprises the first particle after the blast, and
   (3) collecting the deflected blast and the first particle, and
   (4) directing the deflected blast and first particle towards an analyzer.

2. The method of claim 1, wherein the adjusting provides the adjusted air supply with an adjusted humidity that is above an ambient humidity but below a dew point.

3. The method of claim 1, wherein another suitable gas, vapor, or aerosol comprises the adjusted air supply to improve particle extraction from a surface.

4. The method of claim 1, wherein the humidity of the adjusted air supply is from about 80% to about 90% relative humidity.

5. The method of claim 1, wherein the temperature of the adjusted air supply is from about 40° C. to about 43° C.

6. The method of claim 1, wherein the pressure of the adjusted air supply is about 25 psi and the velocity of the adjusted air supply is about 37 m/s.

7. The method of claim 1, wherein the adjusting provides the adjusted air supply with an adjusted temperature that is above an ambient temperature, and below an upper limit.

8. The method of claim 7, wherein the upper limit is a discomfort temperature based upon a pain threshold.

9. The method of claim 7, wherein the upper limit is a destructive temperature which would result in degradation or destruction of the first particle.

10. The method of claim 7, wherein the upper limit is a destructive temperature which would result in degradation or destruction of the surface.

11. An apparatus for extraction of particles from a surface comprising an air adjuster and a probe, wherein the probe comprises an adjusted air supply passage, an adjusted air aperture, a deflected air aperture, and a deflected air passage, and wherein the air adjuster is adapted to provide a flow of an adjusted air supply to the adjusted air supply passage and a blast of adjusted air to the adjusted air aperture, and further adapted to provide the adjusted air supply with an adjusted temperature that is above an ambient temperature, and below an upper limit, and further adapted to provide the adjusted air supply with an adjusted humidity that is above an ambient humidity but below a dew point.

12. The apparatus of claim 11, wherein said flow is continuous.

13. The apparatus of claim 11, wherein said flow is intermittent, pulsed or periodic.

14. The apparatus of claim 11, wherein the adjusted air aperture and the deflected air aperture are configured in proximity, and adapted to allow said blast of adjusted air from the adjusted air aperture to impact an adjacent surface which deflects said blast to produce a deflected blast, and said apparatus is further adapted to allow the deflected air aperture and deflected air aperture to receive the deflected blast and direct the deflected blast to an analyzer.

15. The apparatus of claim 11, wherein the humidity of the adjusted air supply is from about 80% to about 90% relative humidity.

16. The apparatus of claim 11, wherein the temperature of the adjusted air supply is from about 40° C. to about 43° C.

17. The apparatus of claim 11, wherein the pressure of the adjusted air supply is about 25 psi.

18. The apparatus of claim 11, wherein the velocity of the adjusted air supply is about 37 m/s.

19. The apparatus of claim 11, wherein the humidity of the adjusted air supply is from about 80% to about 90% relative humidity, the temperature of the adjusted air supply is from about 40° C. to about 43° C., the pressure of the adjusted air supply is about 25 psi, and the velocity of the adjusted air supply is about 37 m/s.

20. The apparatus of claim 11, wherein the adjusted air supply passage is an extendable, flexible or rigid enclosure around an extraction area on the surface, the adjusted air aperture is adapted to come close to the surface, and the deflected air aperture is adapted to come close to the surface.

* * * * *